United States Patent
Osypka et al.

(10) Patent No.: US 7,192,433 B2
(45) Date of Patent: Mar. 20, 2007

(54) LOCKING VASCULAR INTRODUCER ASSEMBLY WITH ADJUSTABLE HEMOSTATIC SEAL

(75) Inventors: Thomas P. Osypka, Palm Harbor, FL (US); Thomas C. Ries, Tarpon Springs, FL (US); Ernest G. DeBella, Palm Harbor, FL (US); Timothy L. Sass, Fort Richey, FL (US)

(73) Assignee: Oscor Inc., Palm Harbor, FL (US)

( * ) Notice: Subject to any disclaimer, the term of this patent is extended or adjusted under 35 U.S.C. 154(b) by 675 days.

(21) Appl. No.: 10/389,229

(22) Filed: Mar. 14, 2003

(65) Prior Publication Data

US 2003/0216771 A1 Nov. 20, 2003

Related U.S. Application Data

(60) Provisional application No. 60/391,793, filed on Jun. 27, 2002, provisional application No. 60/364,649, filed on Mar. 15, 2002.

(51) Int. Cl.
*A61F 11/00* (2006.01)

(52) U.S. Cl. ............ 606/108; 604/164.05; 604/167.03; 604/170.03; 604/256; 604/537; 604/533

(58) Field of Classification Search ................ 604/506, 604/158, 104–109, 161, 256, 264, 164.01–164.07, 604/164.1, 164.13, 165.01–165.04, 167.01–167.04, 604/167.06, 170.01–170.03, 246–248, 523, 604/537, 533–535, 905; 606/167, 185, 108

See application file for complete search history.

(56) References Cited

U.S. PATENT DOCUMENTS

| | | | |
|---|---|---|---|
| 3,653,388 A | 4/1972 | Tenckhoff | 128/347 |
| 4,166,469 A | 9/1979 | Littleford | 128/784 |
| 4,243,050 A | 1/1981 | Littleford | 128/784 |
| 4,345,606 A | 8/1982 | Littleford | 128/784 |
| 4,362,156 A | 12/1982 | Feller, Jr. et al. | 604/165 |
| 4,451,256 A | 5/1984 | Weikl et al. | 604/164 |
| RE31,855 E | 3/1985 | Osborne | 604/161 |
| 4,581,025 A | 4/1986 | Timmermans | 604/264 |
| 4,596,559 A | 6/1986 | Fleischhacker | 604/170 |
| 4,983,168 A | 1/1991 | Moorehead | 604/161 |
| 5,125,904 A | 6/1992 | Lee | 604/164 |
| 5,250,033 A | 10/1993 | Evans et al. | 604/160 |
| 5,312,355 A * | 5/1994 | Lee | 604/160 |
| 5,338,314 A * | 8/1994 | Ryan | 604/284 |
| 5,389,090 A * | 2/1995 | Fischell et al. | 604/528 |
| 5,409,463 A | 4/1995 | Thomas et al. | 604/167 |
| 5,409,469 A | 4/1995 | Schaerf | 604/282 |
| 5,441,504 A | 8/1995 | Pohndorf et al. | 606/129 |
| 5,478,331 A * | 12/1995 | Heflin et al. | 604/537 |
| 5,536,255 A | 7/1996 | Moss | 604/161 |
| 5,591,137 A * | 1/1997 | Stevens | 604/296 |
| 5,601,540 A * | 2/1997 | Stevens | 604/533 |

(Continued)

*Primary Examiner*—Cris L. Rodriguez
(74) *Attorney, Agent, or Firm*—Scott D. Wofsy; Edwards Angell Palmer & Dodge LLP

(57) ABSTRACT

A vascular introducer assembly is disclosed that includes a dilator, a sheath having an axial lumen for accommodating the dilator, a locking collar for securing the dilator and the sheath to one another and an adjustable hemostatic seal for preventing fluid egress from the axial lumen and restricting insertion of instruments through the axial lumen.

22 Claims, 8 Drawing Sheets

U.S. PATENT DOCUMENTS

| | | | |
|---|---|---|---|
| 5,669,881 A * | 9/1997 | Dunshee | 604/164.1 |
| 5,713,867 A | 2/1998 | Morris | 604/164 |
| 5,741,233 A | 4/1998 | Riddle et al. | 604/165 |
| 5,827,296 A | 10/1998 | Morris et al. | 606/129 |
| 5,836,306 A * | 11/1998 | Duane et al. | 600/585 |
| 5,871,530 A | 2/1999 | Williams et al. | 607/122 |
| 5,951,518 A | 9/1999 | Licata et al. | 604/61 |
| 6,038,472 A | 3/2000 | Williams et al. | 607/5 |
| 6,090,130 A * | 7/2000 | Nash et al. | 606/213 |
| 6,106,487 A * | 8/2000 | Duane et al. | 600/585 |
| 6,178,355 B1 | 1/2001 | Williams et al. | 607/122 |
| 6,251,093 B1 * | 6/2001 | Valley et al. | 604/97.03 |
| 6,336,914 B1 | 1/2002 | Gillespie, III | 604/165.01 |
| 6,352,521 B1 * | 3/2002 | Prosl | 604/167.03 |

* cited by examiner

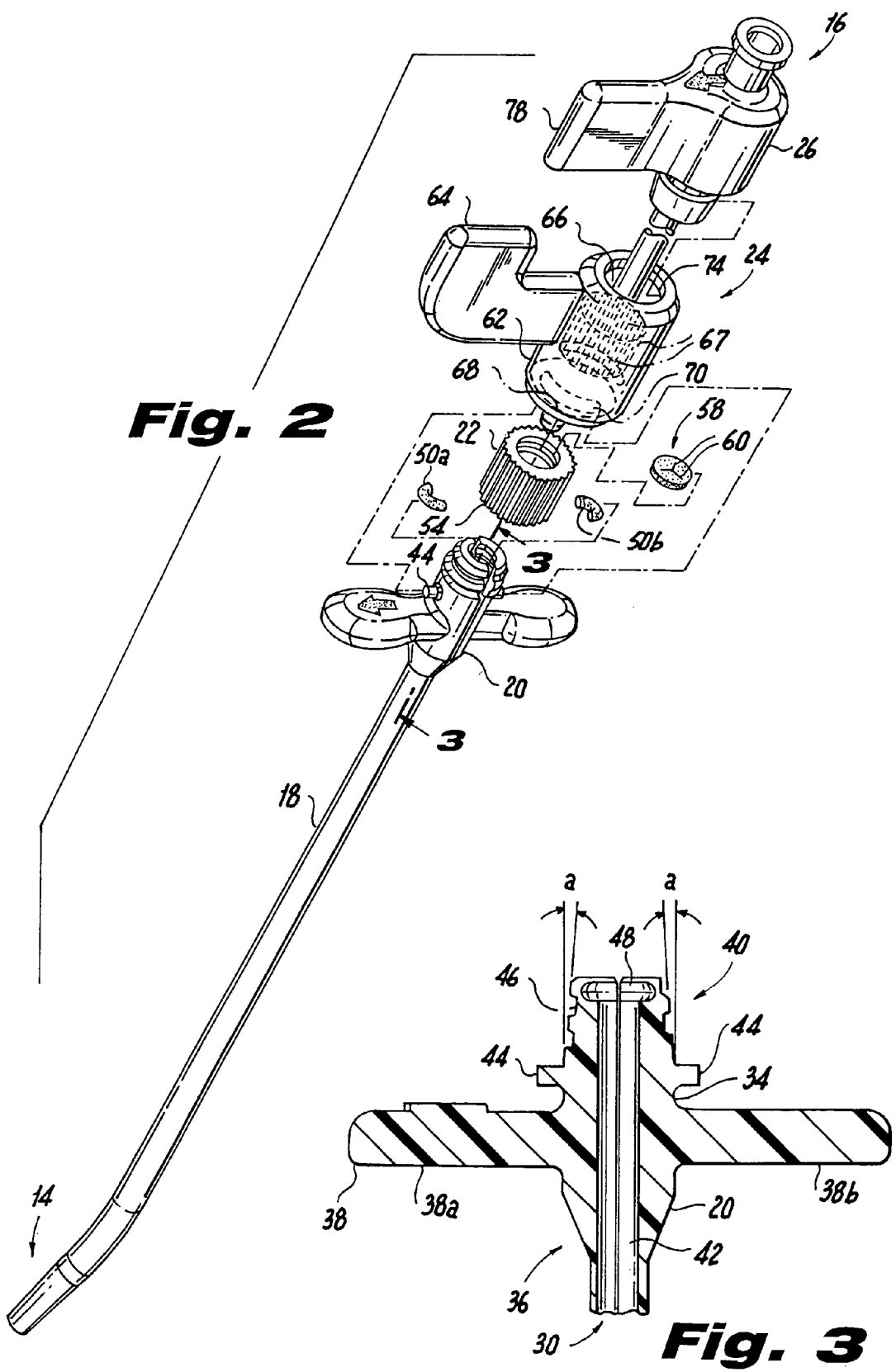

LOCKING VASCULAR INTRODUCER ASSEMBLY WITH ADJUSTABLE HEMOSTATIC SEAL

CROSS-REFERENCE TO RELATED APPLICATION(S)

The subject application claims the benefit of priority to U.S. Provisional Patent Application No. 60/364,649, filed Mar. 15, 2002, and U.S. Provisional Patent Application No. 60/391,793, filed Jun. 27, 2002, the disclosures of which are herein incorporated by reference in their entireties.

BACKGROUND OF THE INVENTION

1. Field of the Invention

The subject disclosure relates to a vascular introducer assembly, and more particularly, to a vascular introducer assembly that includes a dilator, a sheath for accommodating the dilator, a locking mechanism for temporarily securing the dilator and the sheath to one another and an adjustable hemostatic seal for limiting fluid egress from the introducer assembly.

2. Background of the Related Art

The percutaneous introduction of diagnostic and/or therapeutic devices such as pacemaker leads and cardiovascular catheters into a blood vessel is typically accomplished with the aid of an introducer assembly. Introducer assemblies generally include a dilator having a tapered end portion and a thin-walled introducer sheath having a lumen extending therethrough to initially accommodate the dilator, and subsequently accommodate the passage of a pacemaker lead or catheter therethrough.

Typically, the percutaneous introduction of an introducer assembly is accomplished by first inserting a needle into the blood vessel at a desired location and its position is verified by observing fluid return or by a similar method. While the needle is held firmly in place, a guidewire is inserted through the needle caimula to the desired depth. The guidewire is then held in place and the needle is withdrawn. Pressure is applied on the puncture site in order to minimize blood loss. Next, the introducer assembly is threaded over the guide wire. The introducer assembly is grasped close to the skin surface and advanced through the tissue to the desired position. Then, the dilator and guidewire are removed, leaving the sheath installed. A lead, catheter or similar diagnostic or therapeutic device is then introduced into the sheath and advanced to the desired position. Lastly, the sheath is removed, leaving the device disposed within the blood vessel of the patient.

It is known to configure an introducer sheath in such a manner so that it may be easily removed or separated from the lead or catheter after it has been emplaced. For example, it is known to provide score lines in the wall of the sheath to enable the sheath to be pealed away, slit or split open. Once the sheath is removed and catheter is emplaced, therapeutic medical devices such as endocardial pacing/defibrillation leads may be introduced into the blood vessel through the catheter.

Occasionally, the dilator slides out of the sheath during the insertion of the introducer assembly into a blood vessel. This significantly complicates the insertion procedure because the introducer assembly may not slide smoothly into the blood vessel and the insertion may not be effective. In some instances, when the dilator slides out of the sheath during insertion, the sheath may proceed completely through the vein, and break, bend, or tear. Also, if the dilator separates from the central lumen of the sheath, blood may flow undesirably from the vessel through the sheath.

In addition, once the sheath is inserted into a blood vessel, it provides a passage for the free flow of blood. This may result in significant blood loss to the patient. The sheath also provides an open passage for the introduction of air into the vein. This could cause an embolism in the venous system of the patient. To overcome these problems, vascular introducers have been developed with hemostatic valves that prevent the free flow of blood through the introducer sheath.

Examples of such prior art devices are disclosed in U.S. Pat. No. 5,124,904 to Lee and U.S. Pat. No. 5,409,463 to Thomas et al., the disclosures of which are incorporated herein by reference in their entireties. In each of these devices, the hemostatic valve is configured in such a manner so that it creates frictional resistance to the passage of therapeutic devices such as flexible cardiac leads. This makes introduction of the lead difficult and can actually cause damage to the lead.

It would be beneficial therefore, to provide a vascular introducer having a sheath with a hemostatic seal that may be selectively, radially adjusted to accommodate frictionless, unobstructed passage of a diagnostic or therapeutic device therethrough. Furthermore, there is a need for a vascular introducer assembly that provides a mechanism for securely locking the dilator and sheath together during insertion of the introducer assembly to prevent axial movement of the dilator relative to the sheath.

SUMMARY OF THE INVENTION

The present invention provides a vascular introducer which overcomes the problems associated with the prior art.

In particular, the present invention is directed to a vascular introducer which includes an elongated dilator having a tapered distal end portion; an elongated hollow sheath having opposed proximal and distal end portions and an axial lumen extending therethrough to accommodate the dilator; and a selectively adjustable annular seal operatively associated with the proximal end portion of the sheath and configured for movement of the axial lumen between an open position in which the passage of instruments through the axial lumen is unrestricted and a closed position in which insertion of an instrument through the axial lumen is restricted.

The vascular introducer of the present invention may also include a hub which is operatively associated with the proximal end portion of the sheath. This hub has a body portion including an axial passage to accommodate the dilator therein and for being in fluid communication with the axial lumen, a distal end portion and a proximal end portion.

The vascular introducer of the present invention may further include a dilator handle and a locking collar. The dilator handle is configured for directing movement of the dilator relative to the sheath and has a body portion with a proximal portion including a receiving port in communication with the dilator and a distal portion including a tapered stem. The locking collar includes an axial bore therethrough, a proximal portion including an first seating engagement configured for rotatably mounting the tapered stem of the dilator handle therein and a distal portion including a second selectively lockable engagement configured for alternately securing and unsecuring the locking collar with the proximal end portion of the sheath. By securing the locking collar with the sheath, axial movement of the dilator relative to the sheath is restricted.

Preferably, the second selectively lockable engagement on the distal portion of the locking collar includes cooperative interlocking structures defined on the proximal end portion of the sheath and on an inner wall of the locking collar. These cooperative interlocking structures are engaged and disengaged by rotational movement of the locking collar relative to the proximal end portion of the sheath. Furthermore, it is preferable that the movement of the selectively adjustable annular seal between the open position and closed position is actuated by the engagement and disengagment of the locking collar with the proximal end portion of the sheath.

The present invention is also directed to a vascular introducer having an adjustable hemostatic seal. This embodiment of the present invention includes an elongate hollow sheath defining an axial lumen which has opposed proximal and distal end portions; a hub operatively associated with the proximal end portion of the sheath which includes a hub body portion with an axial bore in fluid communication with the axial lumen of the sheath, and a tapered proximal portion having a helical thread defined along an outer periphery thereof and a recessed channel defined circumferentially along an inner periphery thereof; an elastic annular seal disposed within the recessed channel of the hub; and a cap having an axial bore extending therethrough with a helical thread for cooperating with the helical thread of the tapered proximal portion of the hub so that rotational movement of the cap relative to the hub causes the annular seal to move radially relative to the axial bore of the hub.

This embodiment of a vascular introducer constructed in accordance with the present invention may be configured so that the radial movement of the annular seal, which may be fabricated of an elastomeric material such as silicone, is actuated by axial rotation of the cap about a 90 degree arc. Preferably, the aforementioned vascular introducer of the present invention also includes handle members protruding radially from the hub body portion.

In a preferred embodiment of the vascular introducer of the present invention, a trocar seal is disposed about the axial bore of the cap to prevent fluid flow from the lumen and permit insertion of devices through the axial bore of the cap.

The present invention is also directed to a vascular introducer which includes an elongated dilator having a tapered distal end portion and an axial passage extending therethrough; an elongated hollow sheath having opposed proximal and distal end portions and an axial lumen extending therethrough to accommodate the dilator; a hub operatively associated with the proximal end portion of the sheath which includes a hub body portion with an axial passage for accommodating the dilator and being in fluid communication with the axial lumen of the sheath, and a tapered proximal portion; a dilator handle associated with a proximal end of the dilator including a proximal receiving port in communication with the axial passage of the dilator and a distal mounting stem; and a locking collar having an axial bore with a proximal portion configured to receive the distal mounting stem of the dilator handle to facilitate rotation of the dilator handle and a distal portion configured to engage the tapered proximal portion of the hub.

The aforementioned embodiment of a vascular introducer constructed in accordance with the present invention can include cooperative interlocking structures defined on the distal portion of the locking collar and the tapered proximal portion of the hub. Preferably, these cooperative interlocking structures are configured to be engaged by rotational movement of the locking collar relative to the hub about a 90 degree arc through an axial plane. In one embodiment, the cooperative interlocking structures include a pair of pins radially projecting from the tapered proximal portion of the hub and a corresponding pair of receiving slots for the pins defined in an interior wall of the locking collar.

The aforementioned vascular introducer may also include the selectively adjustable annular seal operatively associated with the proximal end portion of the hub and configured for movement of the axial passage between an open position in which the passage of instruments through the axial lumen is unrestricted and a closed position in which insertion of an instrument through the axial lumen is restricted as described above. Preferably, the vascular introducer is configured such that the engagement of the distal portion of the locking collar with the tapered proximal portion of the hub moves the axial passage to the closed position. Even more preferably, the adjustable seal and the cooperative interlocking structures are alternatively engaged and disengaged by rotational movement of the locking collar about a 90 degree arc in the axial plane.

In one embodiment of the present invention, the selectively adjustable annular seal includes a threaded portion defined on the tapered proximal portion of the hub; a circumferential recessed channel defined in an interior wall of the tapered proximal portion of the hub; an annular compressible sealing ring disposed in the circumferential recessed channel of the hub; and a sealing cap having an axial bore and a threaded portion defined therein for being threadably engaged with the threaded portion defined on the tapered proximal portion of the hub, wherein the annular compressible sealing ring in the circumferential recessed channel of the tapered proximal portion of the hub is selectively moved from a compressed position in which fluid egress through the axial passage is restricted and a decompressed position in which fluid egress through the axial passage is unrestricted by alternate threadable engagement of the sealing cap. Preferably, the sealing cap is seated within the axial bore of the locking collar such that alternate rotational movement of the locking collar effectuates the threaded engagement and disengagement of the sealing cap with the tapered proximal portion of the hub.

Further features of the vascular introducer of the subject invention will become more apparent from the detailed description of the present invention that follows taken in conjunction with the drawings.

BRIEF DESCRIPTION OF THE DRAWINGS

So that those having ordinary skill in the art to which the present application appertains will more readily understand how to make and use the same, reference may be had to the drawings wherein:

FIG. 2 is an exploded perspective view of the vascular introducer assembly of FIG. 1 with parts separated for ease of illustration;

FIG. 3 is an enlarged cross sectional view of the hub portion of the vascular introducer assembly of FIG. 1;

These and other features of the vascular introducer assembly of the subject invention will become more readily apparent to those having ordinary skill in the art from the following description of the preferred embodiment.

DETAILED DESCRIPTION OF THE INVENTION

In the following detailed description of the present invention, references are made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. The following detailed description is, therefore, not to be taken in a limiting sense, and the scope of the present invention is defined by the appended claims and equivalents thereof.

Figure 1:
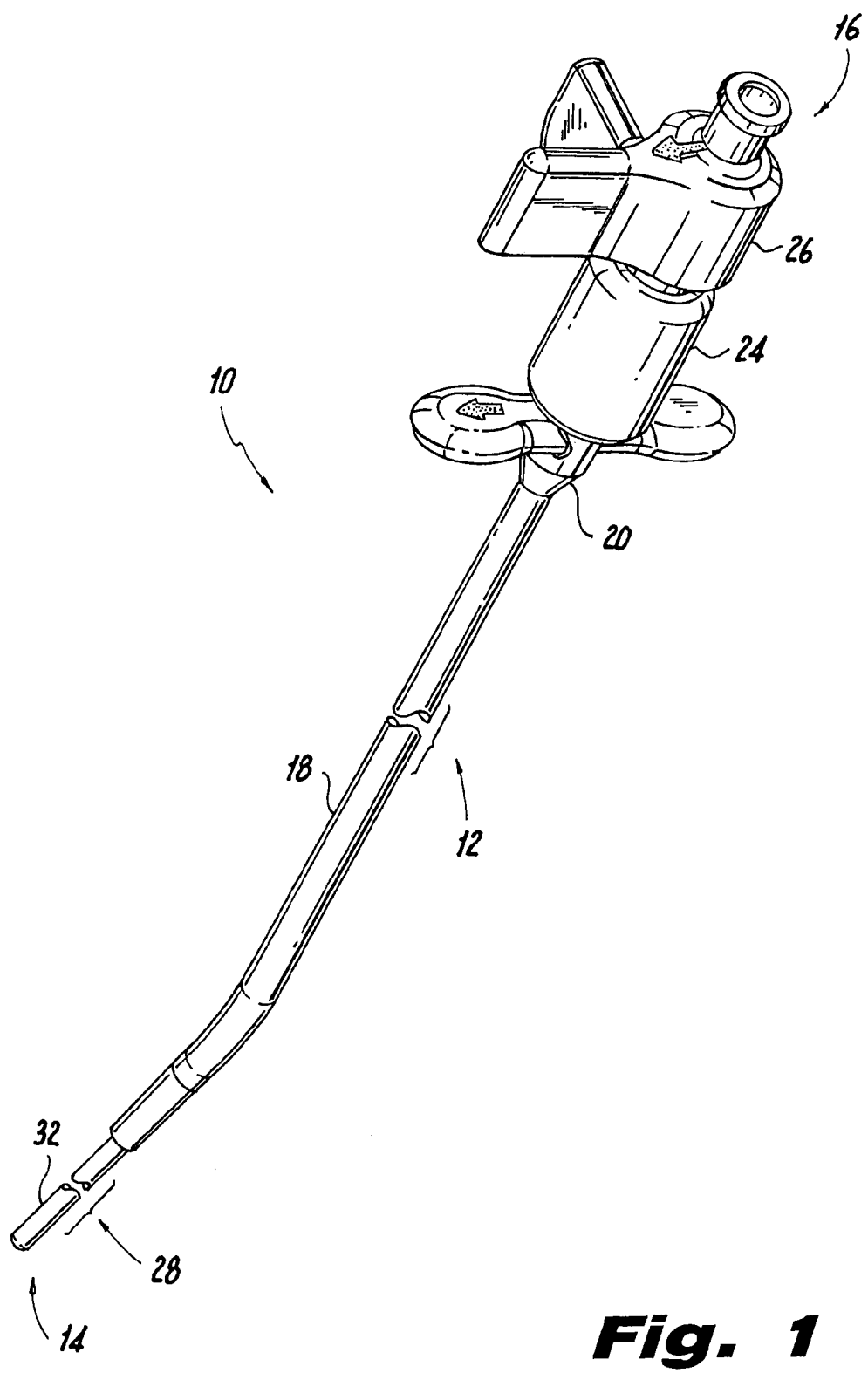
FIG. 1 is a perspective view of a vascular introducer assembly constructed in accordance with a preferred embodiment of the subject invention in a fully assembled condition.

Referring now to the drawings wherein like reference numerals identify similar structural features of the invention, there is illustrated in FIG. 1, a vascular introducer assembly constructed in accordance with a preferred embodiment of the subject invention and designated generally by reference numeral 10. Vascular introducer assembly 10 generally includes an elongated tubular body 12. The general shape and orientation of assembly 10 as shown in FIG. 1 defines a longitudinal axis and an axially opposed distal end 14 and proximal end 16 relative thereto, and these designations will be used as a convention throughout the following description to describe the components and features of the present invention.

Referring now to both FIGS. 1 and 2, this embodiment of introducer assembly 10 has a body 12 that generally includes (listed in order from distal end 14 to proximal end 16) an outer sheath 18, an engagement hub 20, a sealing cap 22, a locking collar 24 and a dilator handle 26, each of which are disposed over a hollow elongate dilator 28 and will be discussed in further detail herein below.

Figure 4:
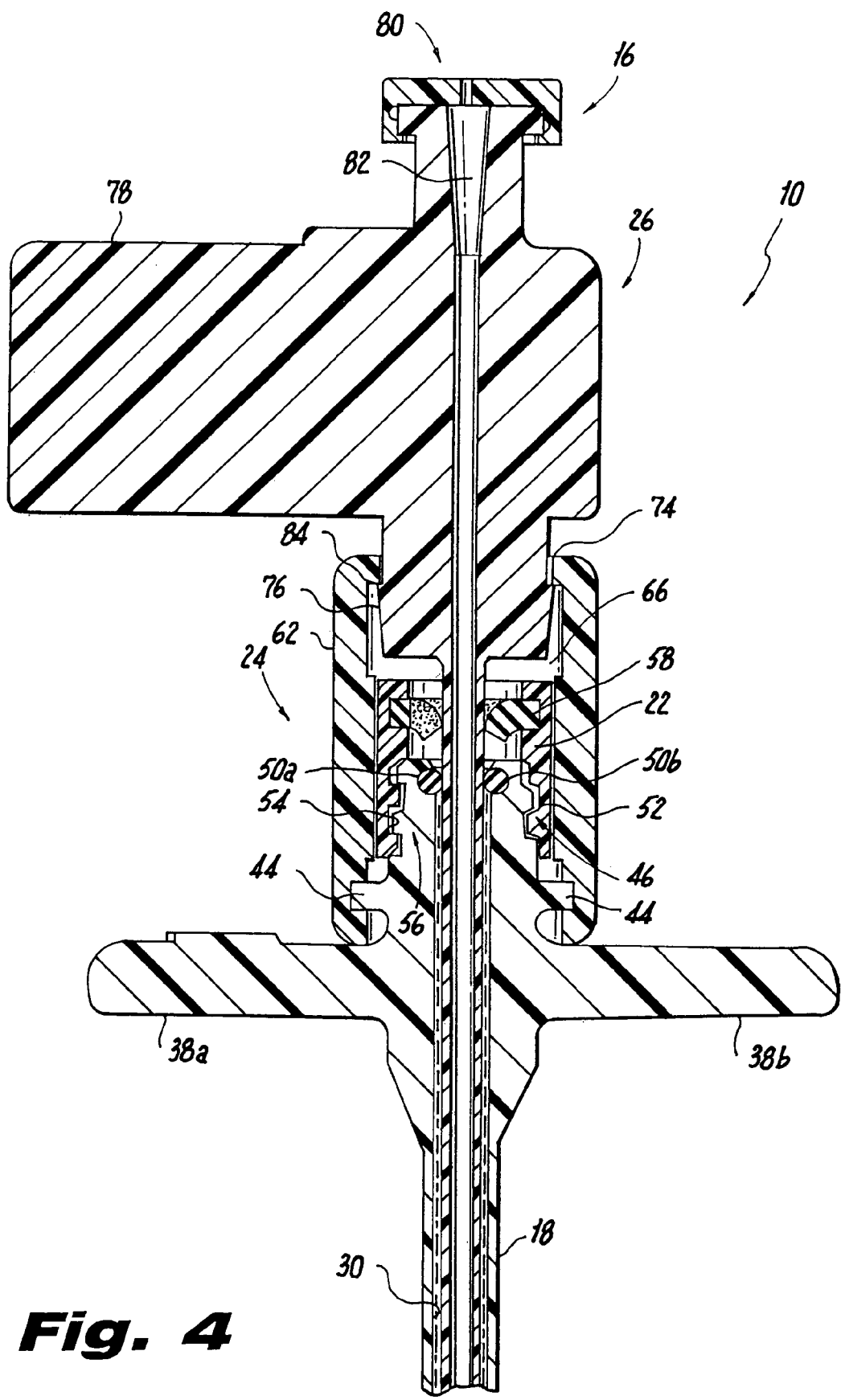
FIG. 4 is an enlarged cross sectional view of the proximal portion of the vascular introducer assembly of FIG. 1 with the rotatable locking collar in a locked position to prevent axial movement of the dilator relative to the sheath and the hemostatic seal in a closed position which restricts access through the axial lumen of the sheath.

Beginning with the distal-most component of assembly 10, outer sheath 18 is hollow and elongate. As shown in FIGS. 3 and 4, outer sheath 18 defines an interior axial lumen 30 for, among other things, accommodating dilator 28. As illustrated in this embodiment, dilator 28 includes a curved distal end portion 32, which, among other things, facilitates endocardial lead placement into areas of the heart that are difficult to access by intravascular means, such as the coronary sinus, but may also be straight or shaped in some other manner as well. Sheath 18 is preferably constructed of a compliant and flexible but resilient material that permits it to assume a curved form corresponding to the curvature of distal end portion 32. Preferably, sheath 18 is fabricated so that its shape may vary depending upon the intended use of the introducer.

Referring now to FIG. 3, along with continuing reference to FIGS. 1 and 2, engagement hub 20 generally includes a central body portion 34 having a tapered distal end portion 36, a sheath handle 38, a tapered proximal end portion 40 and an axial bore 42 therethrough in fluid communication with axial lumen 30. Tapered proximal end portion is sloped inwardly at an angle a, which is preferably between about 1 and about 8 degrees relative to the longitudinal axis defined by introducer 10. In this embodiment, sheath handle 38 includes a pair of opposing, radially outward projecting portions 38a and 38b. Preferably, the axial bore 42 is substantially aligned with and about the same diameter as axial lumen 30.

Proximal end portion 40 is fabricated of a flexible yet resilient material and includes a pair of opposed, radially outward projecting pins 44 positioned distally relative to a threaded portion 46 defined on the exterior of the proximal end portion 40, which is tapered as mentioned above so that its outer diameter generally decreases axially in the proximal direction. A circumferential channel 48 for receiving an annular sealing ring 50 therein is defined along the interior wall of proximal end portion 40 adjacent to its proximal end. Preferably, annular sealing ring 50 is fabricated from a flexible yet resilient material such as silicone. In this embodiment, annular sealing ring 50 includes a pair of semi-circular portions 50a and 50b.

Sealing cap 22 includes a body 52 having axially defined, substantially parallel grooves or flutes defined on its exterior and an axial bore 54 with a threaded portion 56 configured to engage the threaded portion 46 defined on the exterior of proximal end portion 40 of hub 20. Preferably, and as shown with specificity in FIG. 2, cap 22 further includes a trocar seal 58 disposed over axial bore 54 at the proximal end of cap 22. Trocar seal 58 generally consists of a flexible but resilient material having three slits 60 defined therein which extend radially outward from its center to form three flaps.

The three flaps may be forcibly opened to receive the dilator or other device while impeding fluid egress from the sealing cap 22.

Locking collar 24 includes a central body 62 having a single, radially outward projecting L-shaped handle 64 an axial bore 66 for receiving sealing cap 22. In this embodiment, axial bore 66 includes axially defined, substantially parallel grooves or flutes 67 for interlocking with the exterior sealing cap 22 so that rotational movement of collar 24 (i.e., movement not in the axial direction) results in the rotational movement of sealing cap 22 in accordance therewith. Collar 24 also includes a pair of slots 68 that are recessed in the interior wall of body 62 which defines axial bore 66 adjacent to the distal end of collar 24. Slots 68 are configured and dimensioned to receive pins 44 of hub 20 and cooperate together to secure locking collar 24 with the proximal end portion 40 of hub 20. Slots 68 each include an axial portion 70 which extends in the proximal direction along the interior of collar 24 and is joined with a circumferential portion 72 that extends circumferentially along the interior periphery of collar 24. Collar 24 further includes a circular rim 74 defined at the proximal end of central body 56.

Dilator handle 26 includes a tapered distal stem portion 76, a single, radially outward projecting handle 78, a proximal receiving port 80 and an axial bore 82 therein.

Tapered distal stem portion 76 includes a ridge 84 for engaging the circular rim 74 at the proximal end of collar 24 so that dilator handle 26 is rotatably mounted in the proximal end of collar 24. Axial bore 82 is in fluid communication with dilator 28 and proximal receiving port 80, thus, objects or devices such as endocardial leads may be inserted into dilator 28 via proximal receiving port 80.

Figure 5:
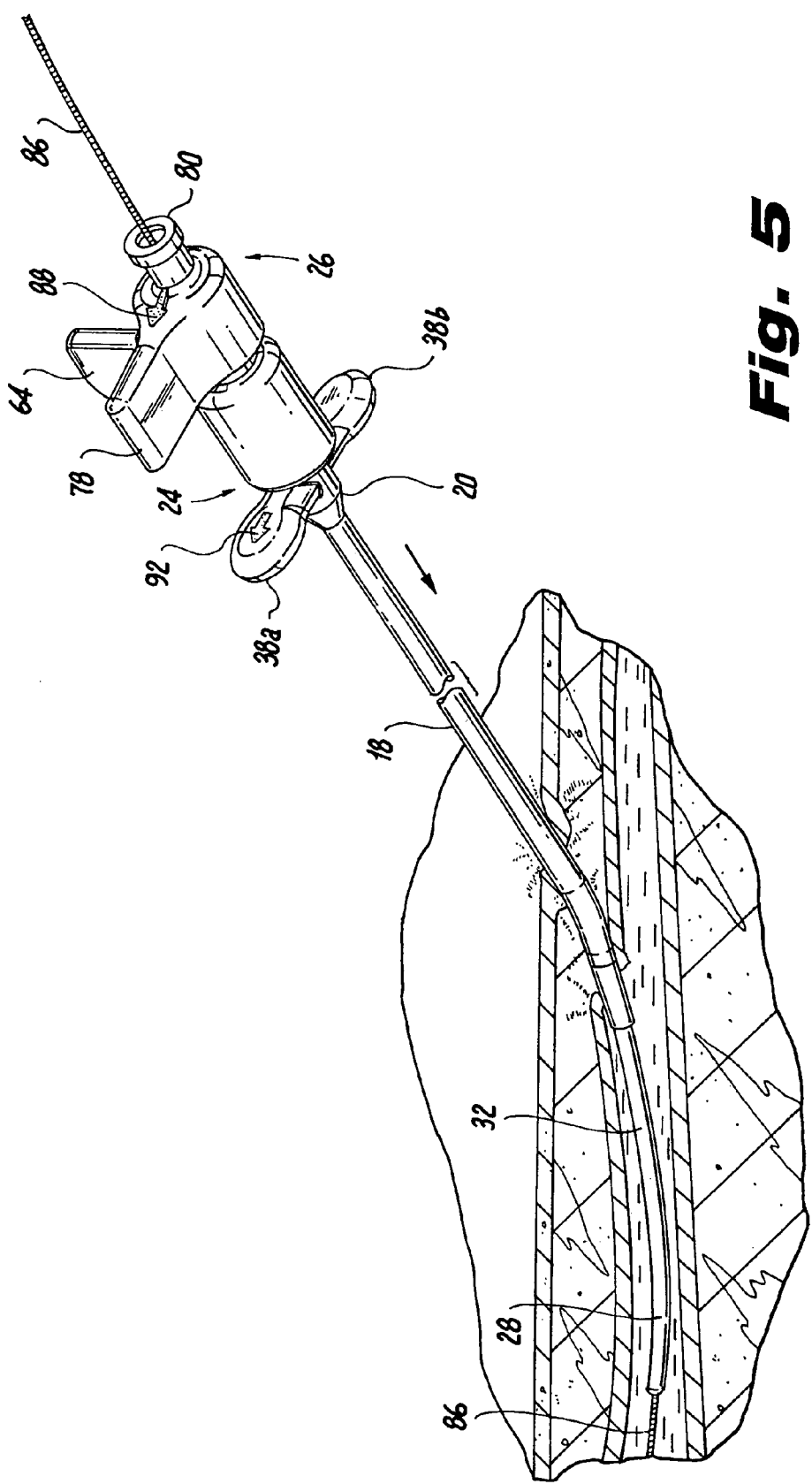
FIG. 5 is a perspective view of the vascular introducer assembly of FIG. 1 being percutaneously introduced into a blood vessel along a guidewire.

In use, the dilator 28 in vascular introducer assembly 10 is inserted over a guidewire 86, as shown in FIG. 5 and as described in the above background section. An arrow 88 is defined radially along the projecting handle 78 of dilator handle 26 to identify the relative direction of the curvature in distal end portion 32 of dilator 28. The locking collar 24, dilator handle 26 and sealing cap 22 cooperate to generally define a rotatable sheath lock and hemostatic seal. As illustrated in FIG. 5, collar 24 is in the locked position on pins 44 (not shown in FIG. 5), which increases the rigidity and stability of the introducer assembly 10 for intravenous insertion, among other things.

As previously noted, rotational movement of collar 24 simultaneously causes the rotation of sealing cap 22, which is interlocked with collar 24 by flutes 67 in axial bore 66. As shown in FIG. 4, placing collar 24 in the locked position (i.e., pins 44 engaged within the circumferential portion 72 of slots 68) rotates sealing cap 22 in the clockwise direction on threaded portion 46 of the tapered proximal end portion 40 of hub 20. By twisting sealing cap 22 clockwise, cap 22 also moves distally with respect to proximal end portion 40, which causes a crimping action that forces proximal end portion 40 radially inward. This action reduces the diameter of axial bore 42 so that the annular sealing ring 50 at the proximal end of axial bore 42 closes around dilator 28, thus, impeding fluid (i.e., blood) flow entering via the distal end of lumen 30 from exiting through bore 42 and restricting insertion of devices into lumen 30.

Figure 6:
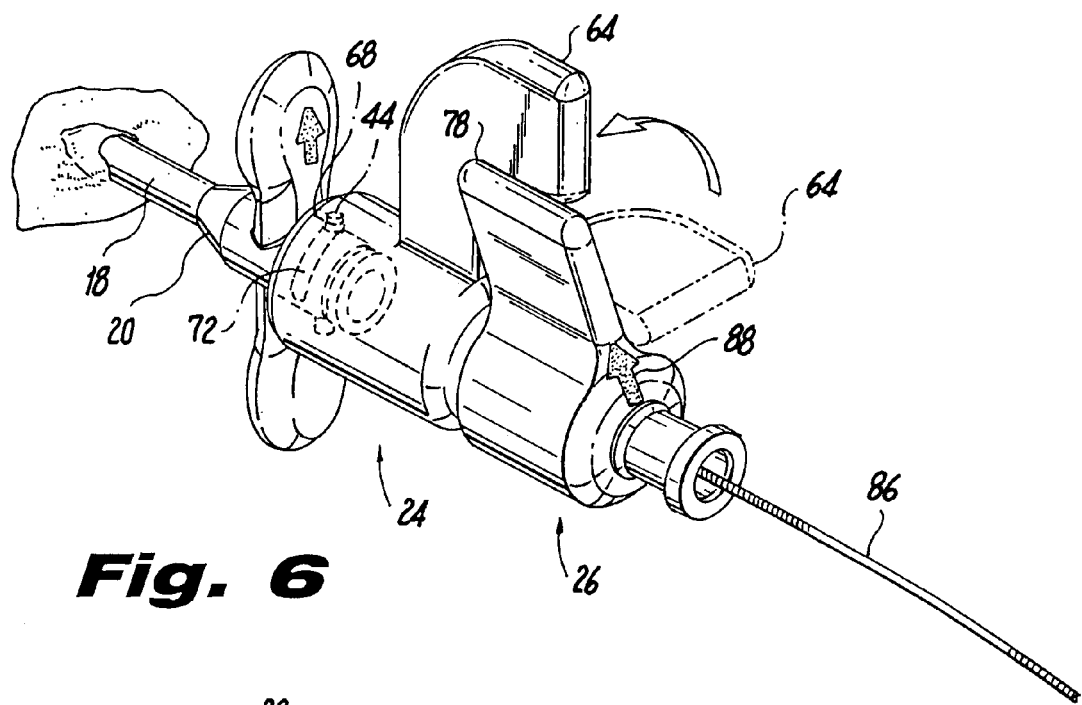
FIG. 6 is a perspective view of the proximal portion of the vascular introducer of FIG. 1 illustrating the rotational movement of the locking collar which moves the hemostatic seal to an open position in which passage of instruments through the axial lumen of the sheath is unrestricted.
Figure 7:
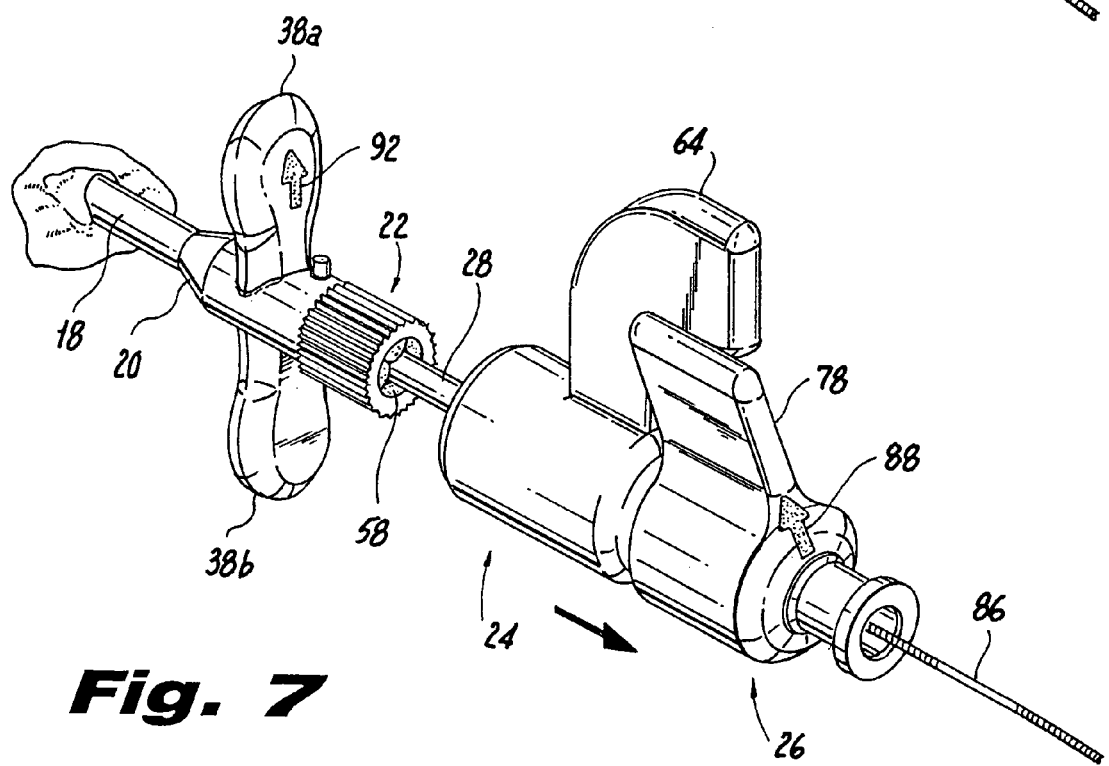
FIG. 7 is a perspective view of the vascular introducer of FIG. 1 illustrating the manner in which the rotatable locking collar and dilator are separated from the sheath and also showing the hemostastic seal which remains intact on the hub portion of the introducer.

Referring now to FIGS. 6 and 7, rotating collar 24 counterclockwise, so that outwardly projecting handle 64 of collar 26 is adjacent handle 78 on dilator handle 26, unlocks pins 44 from slots 68. Sealing cap 22 is also rotated counterclockwise which causes the movement of cap 22 along threaded portion 46 in the proximal direction which releases the aforementioned crimping action. Thus, fluid flow through axial bore 42 is no longer impeded by sealing ring 50. Preferably, the circumferential portions 72 of slots 68 in collar 24 are sufficiently elongated so that collar 24 can be fastened onto pins 44, or unfastened therefrom, by rotating the collar 24 about 90 degrees in either direction.

As shown in FIG. 7, rotating collar 24 to unlock collar 24 from pins 44 in hub 20 allows the collar, along with dilator handle 26 and dilator 28, to move axially and be disengaged from the remaining components (i.e., sealing cap 22, hub 20 and outer sheath 18) in this embodiment of introducer assembly 10.

Figure 8:
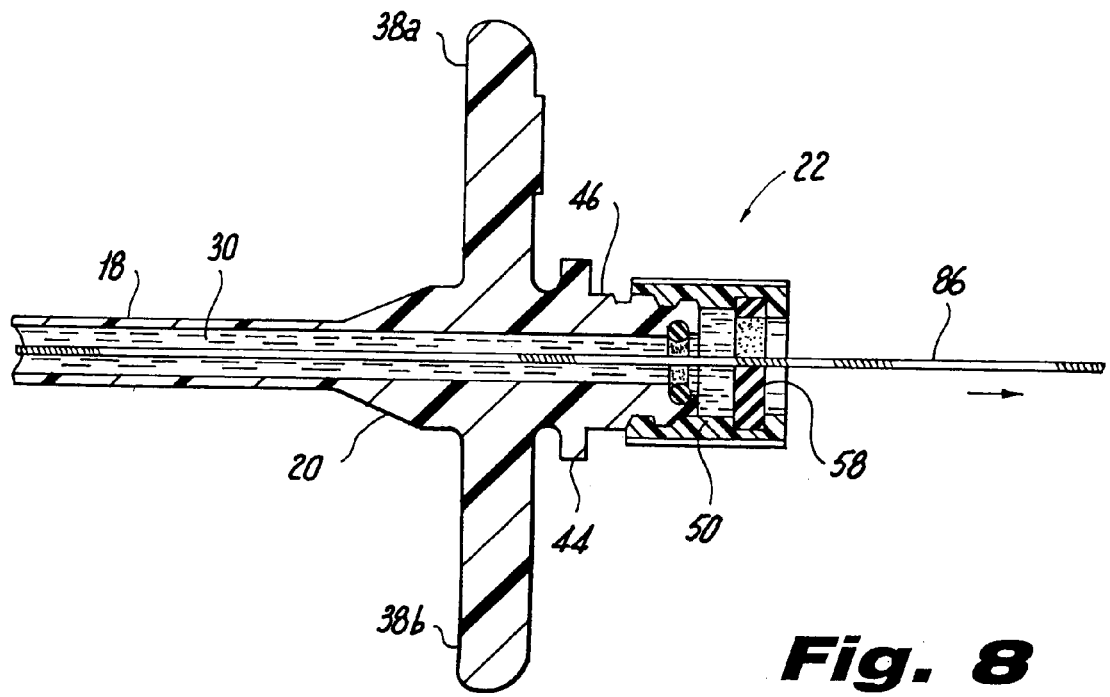
FIG. 8 is a cross sectional view of the hub portion and sealing cap of the vascular introducer assembly of FIG. 1 after the rotatable locking collar and dilator have been removed therefrom to illustrate the components of the present invention forming the adjustable hemostatic seal, with the seal being disposed in an open position in which passage of instruments through the axial lumen of the sheath is unrestricted.
Figure 9:
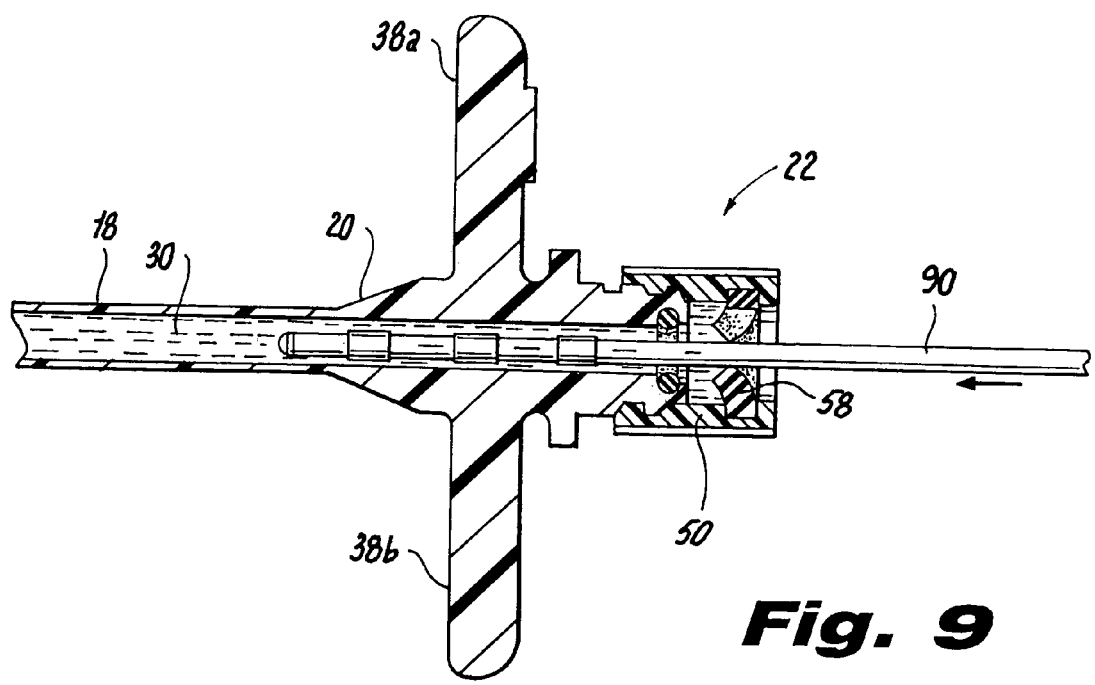
FIG. 9 is a cross sectional view of the hub portion and sealing cap as shown in FIG. 1, which illustrates the valve in an open position with an endocardial lead being inserted through the trocar seal of the sealing cap.
Figure 10:
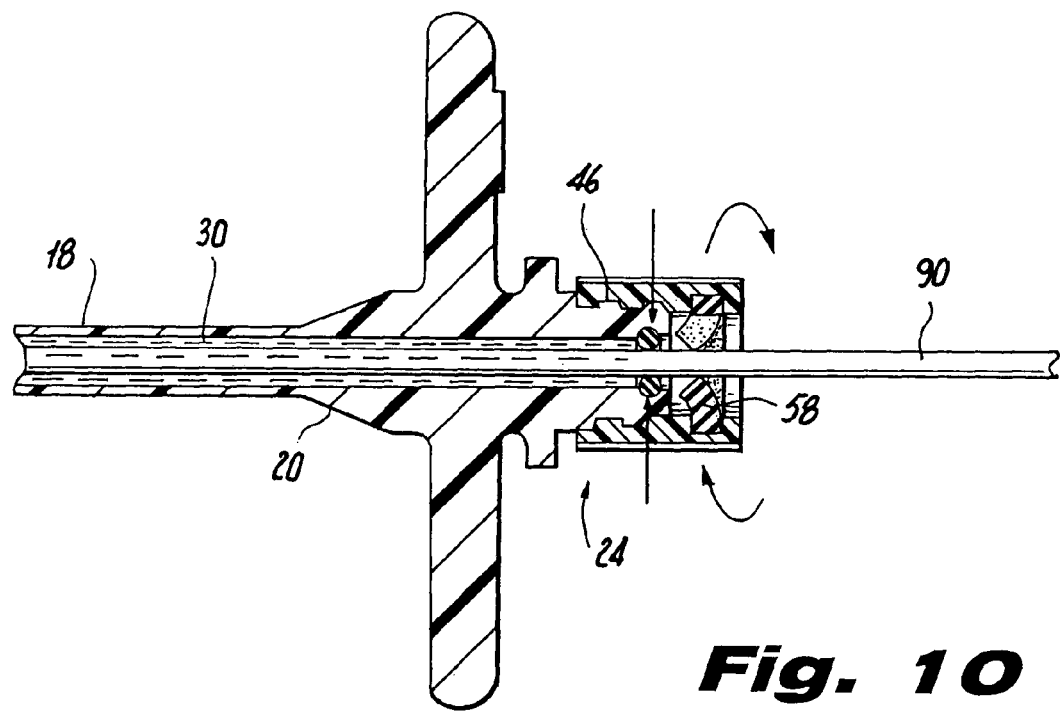
FIG. 10 is a cross sectional view of the hub portion and sealing cap shown in FIG. 9, along with the dilator disposed in the lumen of the introducer assembly, illustrating the movement of the sealing cap relative to the hub so that the hemostatic seal radially compresses around the dilator.

As shown in FIGS. 8 and 9, trocar seal 58 inhibits fluid flow entering lumen 30 from exiting cap 22 when collar 24, dilator handle 26 and dilator 28 are removed from introducer assembly 10. This allows guidewire 86 to be removed so that introducer assembly 10 may be used to insert devices or equipment, such as an endocardial lead 90, intravenously through lumen 30. In addition, dilator 28 and other associated components may be reinserted through lumen 30, and cap 22 may be threaded onto threaded portion 46 thereafter so that the aforementioned crimping action is applied, as shown in FIG. 10.

Figure 11:
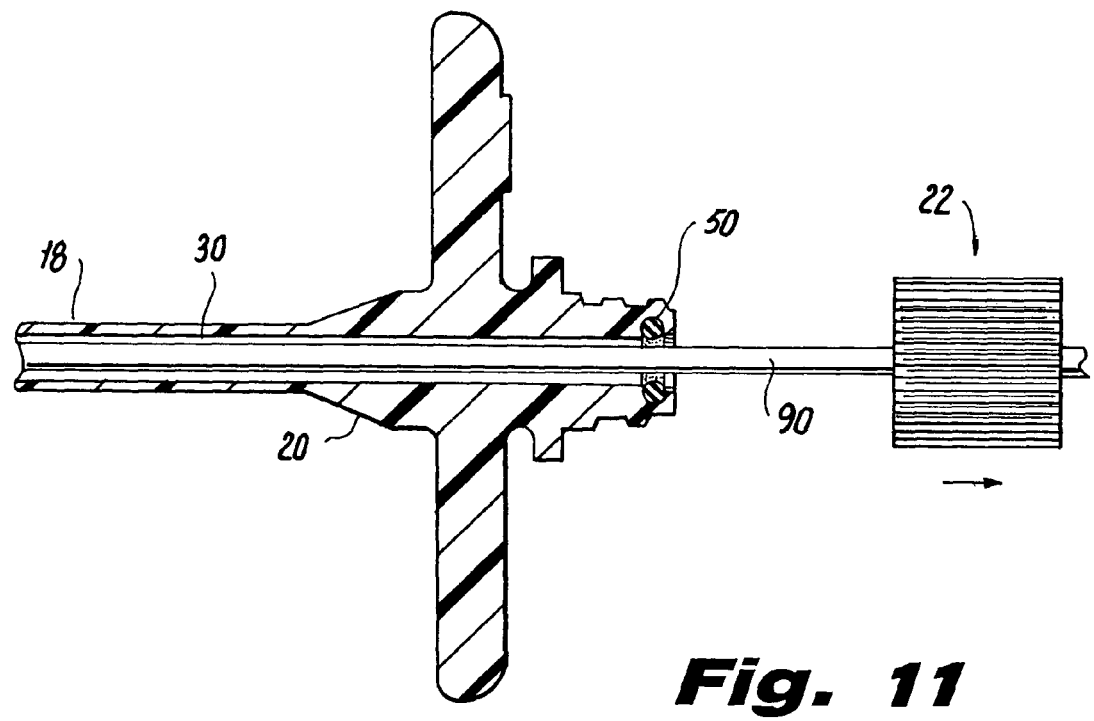
FIG. 11 is a cross sectional view of the hub portion of FIG. 10 illustrating the manner in which the sealing cap is removed from the hub when the hemostatic seal is in an open position.
Figure 12:
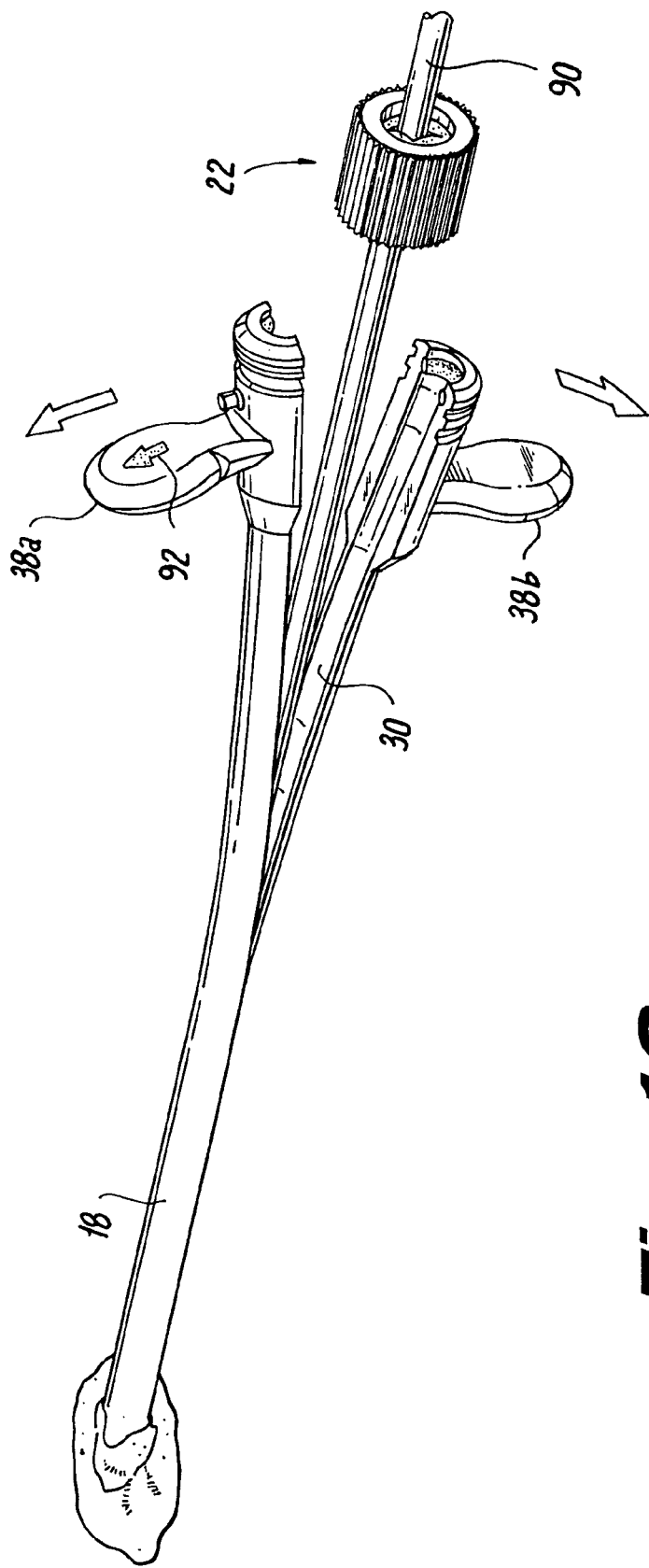
FIG. 12 is a perspective view of the vascular assembly of the subject invention illustrating the manner in which the sheath is split along score lines to facilitate removal from the operative site.

As illustrated in FIG. 11, cap 22 may be threaded off and removed from hub 20. As described in the background section, this is essentially the first step in the removal of the introducer assembly 10, and facilitates removal of outer sheath 18 and hub 20. As shown in FIG. 12, in this embodiment, outer sheath 18 and hub 20 can be split substantially in half by pulling both handles 38a and 38b of hub 20 apart in opposing radial directions. Handle 38a is marked with an arrow 92 pointing in the radial direction as a guide. Preferably, outer sheath 18 and hub 20 are constructed with axially opposing weakened zones or score lines that facilitate dividing sheath 18 as shown in FIG. 12, without compromising the integrity of sheath 18 or restricting use of sheath 18 for any of its intended purposes.

While the invention has been described with respect to preferred embodiments, those skilled in the art will readily appreciate that various changes and/or modifications can be made to the invention with departing from the spirit or scope of the invention.

What is claimed is:

1. A vascular introducer assembly comprising:
   a) an elongated dilator having a tapered distal end portion;
   b) an elongated hollow sheath having opposed proximal and distal end portions and an axial lumen extending therethrough to accommodate the dilator; and
   c) a selectively adjustable annular seal operatively associated with the proximal end portion of the sheath and configured for radial movement between an open position in which passage of an instrument through the axial lumen of the sheath is unrestricted and a closed position in which insertion of an instrument through the axial lumen of the sheath is restricted; and
   d) score lines longitudinally disposed on a wall of the sheath to facilitate splitting of the sheath.

2. A vascular introducer assembly as recited in claim 1, further comprising a hub operatively associated with the proximal end portion of the sheath, the hub having a body portion including an axial passage to accommodate the dilator therein and for being in fluid communication with the axial lumen, a distal end portion and a proximal end portion.

3. A vascular introducer assembly as recited in claim 1, further comprising:
   a dilator handle configured for directing movement of the dilator relative to the sheath and having a body portion with a proximal portion including a receiving port in communication with the dilator and a distal portion including a tapered stem; and a locking collar having an axial bore therethrough, a proximal portion including a first seating engagement configured for rotatably mounting the tapered stem of the dilator handle therein and a distal portion including a second selectively lockable engagement configured for alternately securing and unsecuring the locking collar with the proximal end portion of the sheath to restrict axial movement of the dilator relative to the sheath.

4. A vascular introducer assembly as recited in claim 3, wherein the second selectively lockable engagement on the distal portion of the locking collar includes cooperative interlocking structures defined on the proximal end portion of the sheath and on an inner wall of the locking collar, the cooperative interlocking structures being engaged and disengaged by rotational movement of the locking collar relative to the proximal end portion of the sheath.

5. A vascular introducer assembly as recited in claim 4, wherein movement of the selectively adjustable annular seal between the open position and closed position is actuated by the engagement and disengagment of the locking collar with the proximal end portion of the sheath.

6. A vascular introducer assembly having an adjustable hemostatic seal comprising:

a) an elongated hollow sheath defining an axial lumen, the sheath having opposed proximal and distal end portions;

b) a hub operatively associated with the proximal end portion of the sheath, the hub including a hub body portion with an axial bore in fluid communication with the axial lumen of the sheath and a tapered proximal portion having a helical thread defined along an outer periphery thereof, a recessed channel defined circumferentially along an inner periphery thereof, and handle members protruding radially outward from the hub body portion, wherein the handle members are radially opposed from one another relative to the axis of the hub body portion;

c) an elastic annular seal disposed within the recessed channel of the hub; and d) a cap having an axial bore extending therethrough with a helical thread for cooperating with the helical thread of the tapered proximal portion of the hub so that rotational movement of the cap relative to the hub causes the annular seal to move radially relative to the axial bore of the hub.

7. A vascular introducer assembly as recited in claim 6, wherein the radial movement of the annular seal is actuated by axial rotation of the cap about a 90 degree arc.

8. A vascular introducer assembly as recited in claim 6, wherein the annular seal is fabricated of an elastomeric material.

9. A vascular introducer assembly as recited in claim 6, wherein the annular seal is fabricated of silicone.

10. A vascular introducer assembly as recited in claim 6, further comprising a trocar seal disposed about the axial bore of the cap for preventing fluid flow from the lumen and permitting insertion of devices through the axial bore of the cap.

11. A vascular introducer assembly comprising:

a) an elongated dilator having a tapered distal end portion and an axial passage extending therethrough;

b) an elongated hollow sheath having opposed proximal and distal end; portions and an axial lumen extending therethrough to accommodate the dilator;

c) a hub operatively associated with the proximal end portion of the sheath, the hub including a hub body portion with an axial passage for accommodating the dilator and being in fluid communication with the axial lumen of the sheath, and having a tapered proximal portion;

d) a dilator handle associated with a proximal end of the dilator including a proximal receiving port in communication with the axial passage of the dilator and a distal mounting stem; and e) a locking collar having an axial bore with a proximal portion configured to receive the distal mounting stem of the dilator handle to facilitate rotation of the dilator handle and a distal portion configured to engage the tapered proximal portion of the hub.

12. A vascular introducer assembly as recited in claim 11, wherein the distal portion of the locking collar and the tapered proximal portion of the hub include cooperative interlocking structures defined respectively thereon.

13. A vascular introducer assembly as recited in claim 12, wherein the cooperative interlocking structures are configured to be engaged by rotational movement of the locking collar relative to the hub about a 90 degree arc through an axial plane.

14. A vascular introducer assembly as recited in claim 12, wherein the cooperative interlocking structures include a pair of pins radially projecting from the tapered proximal portion of the hub and a corresponding pair of receiving slots for the pins defined in an interior wall of the locking collar.

15. A vascular introducer assembly as recited in claim 11, further comprising a selectively adjustable annular seal operatively associated with the proximal end portion of the hub and configured for movement of the axial passage between an open position in which the passage of instruments through the axial lumen is unrestricted and a closed position in which insertion of an instrument through the axial lumen is restricted.

16. A vascular introducer assembly as recited in claim 15, wherein engagement of the distal portion of the locking collar with the tapered proximal portion of the hub moves the axial passage to the closed position.

17. A vascular introducer assembly as recited in claim 15, wherein the adjustable seal and the cooperative interlocking structures are alternatively engaged and disengaged by rotational movement of the locking collar about a 90 degree arc in the axial plane.

18. A vascular introducer assembly as recited in claim 15, wherein the selectively adjustable annular seal includes:

a) a threaded portion defined on the tapered proximal portion of the hub;

b) a circumferential recessed channel defined in an interior wall of the tapered proximal portion of the hub;

c) an annular compressible sealing ring disposed in the circumferential recessed channel of the hub; and d) a sealing cap having an axial bore and a threaded portion defined therein for being threadably engaged with the threaded portion defined on the tapered proximal portion of the hub, wherein the annular compressible sealing ring in the circumferential recessed channel of the tapered proximal portion of the hub is selectively moved from a compressed position in which fluid egress through the axial passage is restricted and a decompressed position in which fluid egress through the axial passage is unrestricted by alternate threadable engagement of the sealing cap.

19. A vascular introducer assembly as recited in claim 18, wherein the sealing cap is seated within the axial bore of the locking collar such that alternate rotational movement of the locking collar effectuates the threaded engagement and disengagement of the sealing cap with the tapered proximal portion of the hub.

20. A vascular introducer assembly comprising:
   a) an elongated dilator having a tapered distal end portion;
   b) an elongated splitable sheath having opposed proximal and distal end portions and having an axial lumen extending therethrough to accommodate the dilator;
   c) a handle portion operatively associated the proximal end portion of the sheath and including a splitable central hub forming a passageway into the central lumen of the sheath, the handle portion including diametrically opposed handle members extending radially outward from the central hub;
   d) a two-part annular seal disposed within the splitable central hub of the handle portion for interacting with the dilator; and
   e) means for radially compressing the annular seal around the dilator.

21. A vascular introducer assembly as recited in claim 20, wherein the means for radially compressing the annular seal around the dilator includes a threaded collar mounted for axial rotation on the central hub of the handle portion to facilitate radial compression of the central hub.

22. A vascular introducer assembly as recited in claim 20, wherein the diametrically opposed handle members are adapted and configured to be pulled radially outward to facilitate splitting of the central hub.

* * * * *